United States Patent
Klett

(10) Patent No.: US 8,908,023 B2
(45) Date of Patent: Dec. 9, 2014

(54) METHOD AND DEVICE FOR THE RECORDING OF BODY MOVEMENTS

(75) Inventor: Rolf Klett, Hochbarg (DE)

(73) Assignee: Dental Innovation GmbH, Dortmund (DE)

( * ) Notice: Subject to any disclaimer, the term of this patent is extended or adjusted under 35 U.S.C. 154(b) by 1232 days.

(21) Appl. No.: 12/162,221

(22) PCT Filed: Jan. 23, 2007

(86) PCT No.: PCT/DE2007/000146
§ 371 (c)(1), (2), (4) Date: Dec. 3, 2008

(87) PCT Pub. No.: WO2007/085241
PCT Pub. Date: Aug. 2, 2007

(65) Prior Publication Data
US 2009/0179986 A1    Jul. 16, 2009

(30) Foreign Application Priority Data

Jan. 26, 2006 (DE) .......... 10 2006 003 945
Jan. 27, 2006 (DE) .......... 10 2006 004 197

(51) Int. Cl.
H04N 7/18 (2006.01)
A61B 5/11 (2006.01)
G06T 7/00 (2006.01)
G06K 9/00 (2006.01)
A61B 5/00 (2006.01)
A61C 19/045 (2006.01)

(52) U.S. Cl.
CPC .............. A61B 5/1114 (2013.01); G06T 7/0042 (2013.01); A61C 19/045 (2013.01);
(Continued)

(58) Field of Classification Search
CPC .... A61B 5/107; A61B 5/1127; G06F 3/0346; G06F 3/017; G06F 3/011; A61C 19/045; G06K 9/00342; A63B 2071/0647; A63B 24/0021; G06T 2207/30204; G06T 17/00; G06T 19/00
USPC ....... 433/69; 356/614; 600/587, 590; 348/77, 348/155, 157
See application file for complete search history.

(56) References Cited

U.S. PATENT DOCUMENTS 5,459,793 A * 10/1995 Naoi et al. ............. 382/165
7,347,690 B2 * 3/2008 Jordan et al. ........... 433/69
(Continued)

FOREIGN PATENT DOCUMENTS

DE      4411907 A1   10/1995
WO   WO 2004/023783 A2   3/2004

OTHER PUBLICATIONS

"PCT International Search Report dated Jun. 17, 2007 for PCT/DE2007/000146, from which the instant application is based," 2 pgs.
(Continued)

Primary Examiner — Peling Shaw
(74) Attorney, Agent, or Firm — Fredrikson & Byron, P.A.

(57) ABSTRACT

The invention relates to a method for recording the position, location or movement of a body part of a patient and a device for recording the position, location or movement of a body part or a medical instrument. According to the invention, a graphic marker is connected with the body part or the instrument and an image of the body comprising the graphic marker is generated by an image recording camera. The image is processed by a processor device as an image file. The invention is characterized in that at least one geometric size characteristic of the graphic marker is known, wherein the processor device determines the position, location and/or movement of the graphic marker in the three-dimensional space and in quantitative manner relative to the image recording camera by means of the known size characteristic. The invention offers, without the need of manual calibration of the measuring system, a substantial automatization and a high measuring precision during the determination of position and movement in the three-dimensional space. Simultaneously, the expenditure on equipment can be reduced and the reaction to the object or body part to be measured or to the patient can be minimized.

34 Claims, 1 Drawing Sheet

(52) U.S. Cl.
CPC ......... *G06K 9/00342* (2013.01); *A61B 2562/08* (2013.01); *A61B 5/4528* (2013.01); *A61B 5/4542* (2013.01); *A61B 2562/046* (2013.01); *A61B 5/1127* (2013.01)
USPC .......................................................... 348/77

(56) References Cited

U.S. PATENT DOCUMENTS

| | | | | |
|---|---|---|---|---|
| 2003/0012423 | A1* | 1/2003 | Boland et al. | 382/154 |
| 2003/0063292 | A1* | 4/2003 | Mostafavi | 356/614 |
| 2005/0075585 | A1* | 4/2005 | Kim et al. | 600/590 |
| 2007/0292004 | A1* | 12/2007 | Peters | 382/120 |

OTHER PUBLICATIONS

"PCT Written Opinion dated Jun. 17, 2007 and English Translation for PCT/DE2007/000146, from which the instant application is based," 9 pgs.

"PCT International Preliminary Report on Patentability dated Jul. 28, 2008 and English Translation for PCT/DE2007/000146, from which the instant application is based," 12 pgs.

* cited by examiner

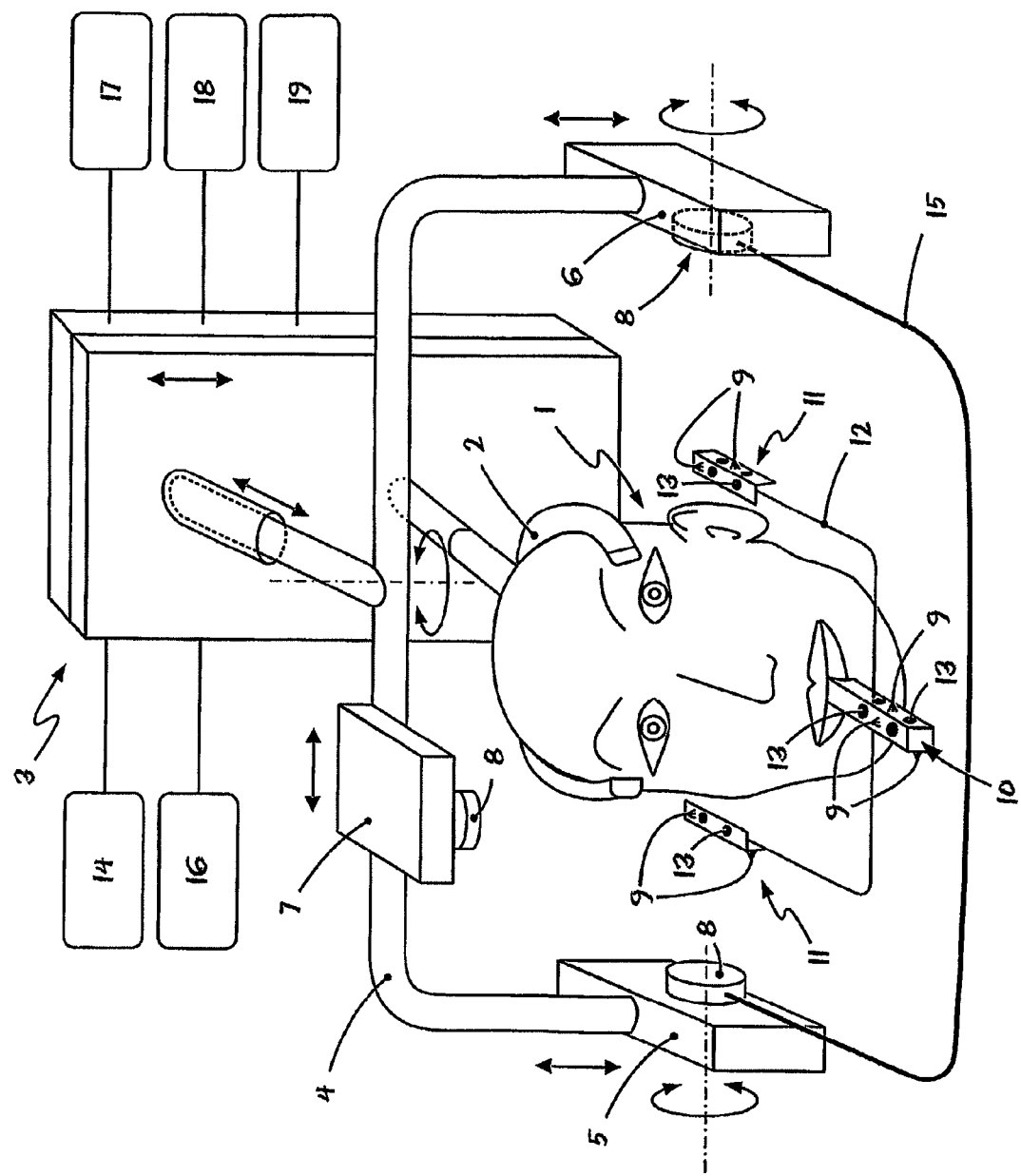

METHOD AND DEVICE FOR THE RECORDING OF BODY MOVEMENTS

RELATED APPLICATIONS

This application is a 35 U.S.C. 371 national stage filing from International Application No. PCT/DE2007/00146 filed Jan. 23, 2007, which claims priority to German Application 10 2006 004 197.6 filed Jan. 27, 2006 and German Application No. 10 2006 003 945.9 filed Jan. 26, 2006, the teachings of all which are incorporated herein by reference.

The invention relates to a method for recording of position, location or movement of a body part of a patient by means of electronic image recognition and a device for recording of position, location or movement of a body part of a patient or a medical instrument.

Methods for recording of the position, the spatial location, or of movement paths, at least of parts of the human body, or in general of body parts of patients or corresponding devices, respectively, are employed in a variety of different fields, based, for example, on science and research, from the medical field to media production.

It is, for example, known to record position, location or movement of body limbs by means of mechanical or electromechanical detectors, and to transfer the obtained data preferably to electronic processor and storage media. This way it is possible to generate, for example, movement evaluations within the scope of the training supervision of athletes; it is possible, based on the obtained position and movement data, to control mechanical actuators such as robot arms or to generate digital visualizations in the film and media field; or the obtained data are used, for example, for support at the medical diagnosis or therapy.

Besides the mechanical or electromechanical detectors for determination of position, location or movement of body limbs or body parts, furthermore contactless detector systems operating, for example, optically or with ultrasound and the like, are known. In case of such known contactless detector systems, the body parts to be evaluated are generally first provided with easily traceable reflectors or illuminating points, such as, for example, glued on light-emitting diodes or the like. Subsequently the movement sequence to be studied is recorded by pointing a sensor unit or an image recording camera, respectively, towards the body parts provided with the illuminating points, and then generating corresponding film or image records, respectively, of the body parts or illuminating points, respectively.

Moreover, in the medical field, devices are known for detection of the position and for navigation, respectively, of medical instruments, for example surgical instruments, the position or the movement path of which is traced in a similar manner at least by portions of the medical instrument. Hereby the surgeon is enabled, for example by means of a manually controlled manipulator, to a more precise working than by hand because by the manipulator, the medical instrument can be directed more precisely due to the position tracing and due to a movement transmission, and inaccuracies or shaking of the surgeon can be compensated hereby. In addition, such devices for detection of the position or for navigation, respectively, of medical instruments are used in so-called robot medicine, for example for the automatically controlled milling of the femoral neck for the purpose of the subsequent anchoring of a hip joint endoprosthesis.

Such known methods and devices, respectively, for recording of position, location or movement of body parts of patients and devices, respectively, for movement tracing of medical instruments are, however, on the one hand in most cases complicated, and moreover, allow at best a medium accuracy with respect to the determination of the position or the spatial location, respectively, when recording. For increasing the accuracy, in case of the known methods or devices, respectively, it is uniformly necessary to calibrate the relative position between the traced body part or instrument and the tracing sensor system in a complicated manner, in order to thereby be able to make the desired exact quantitative statements about the location or the movement curves, respectively, of the traced body parts or instruments, wherein additionally with each major change between the traced body part or instrument and the tracing sensor system, a new calibration is necessary to eliminate measurement errors.

With this background it is the object of the present invention to provide a method for recording of position, location or movements of body parts and a device for position and movement tracing, respectively, of body parts or medical instruments, whereby the mentioned existing drawbacks of the prior art are resolved. More preferably, hereby a high degree of automatization as well as a very high accuracy of position determination is to be achieved; the method and the device are further to be used with a particularly low equipment expenditure having a particularly high flexibility at the same time, and the reaction on the object or body part and on the patient, respectively, through the recording and measurement, respectively, is to be minimized.

The method according to the invention serves for recording of position, location or movement of at least one part of a body of a patient. For the purpose of simplicity and unity the term "patient" is used consistently, wherein hereby, however, no limitation of the invention to medical fields is implied. Moreover, the term "patient" in the context of the present invention is to be understood as in the broadest sense as a synonym for "living creature to be observed".

Here the at least one part of the body of the patient first is arranged in an object space and can be imaged by means of at least one image recording camera into an image space. The differentiation in "object space" and "image space" is made here to be able to make a clear conceptual differentiation between the geometrical relationships at the object or the patient, respectively, on the one hand (object space), and the geometrical relationships within the image (image space) generated by the image recording camera.

Within the scope of the method according to the invention, here in a first process step a) at least one graphic marker is connected with at least one body part of the patient. In this case, at least one geometrical size characteristic of the graphic marker is known. Only as an illustrative, but by no means limiting example for such a graphic marker to be connected with the body part of the patient, a circular glued marker is mentioned as the simplest case, wherein in case of the simple circular marker the size characteristic consists in the known diameter of the circular marker in the object space.

In a further process step b), an image of at least the area of the body part comprising the graphic marker is then generated by the image recording camera.

Then, in a further process step c), a transfer of the image as an image file, for example a pixel image, from the image recording camera into an electronic storage or processor device, respectively, is carried out.

In a further process step d), within the image space of the image file, an automatic localization of the image of the graphic marker contained in the image file is then carried out by means of an application of an image recognition procedure by the processor device to the image file.

During a further process step e), then the size characteristic of the graphic marker in the image space is determined. This means, in the above mentioned example of the simple circular marker used as the graphic marker, that by the processor device in this process step, for example, it is determined to how many image pixels strung together (if the image file exists in the form of a pixel image) the diameter of the image of the circular marker in the image file is equal to.

In a further process step f), then the position and/or the location of the graphic marker in the object space relative to the image recording camera is determined. This takes place on the basis of the size characteristic of the graphic marker now known in the object space as well as in the image space. In other words, in this process step, an automatic calibration of the image recording camera takes place with respect to each of the present geometrical relationships between the location of the image recording camera and the location of the body part or the location of the graphic marker arranged thereon, respectively.

Through the size characteristic known in the object space as well as in the image space (example: the circular marker has the known diameter "20 mm" in the object space and at the same time the determined diameter "328 pixel" in the image space), in consideration of the imaging properties of the camera lens, the actual distance between the graphic marker and the image recording camera, as well as the distance between the graphic marker and the optical axis of the image recording camera can be determined. In addition, a potential angle-tilting of the graphic marker relative to the optical axis of the image recording camera can be determined. In the example of the simple circular marker, this can take place on the basis of the readily possible detection of the two half-axes of the generally elliptical image of the circular marker in the image space.

The method according to the invention thereby allows the determination of the position in three-dimensional space as well as the detection of the angular position of the body part or the graphic marker connected with the body part, respectively, relative to the image recording camera, without the necessity of a manual calibration of the camera. Thereby, basically a plurality of possible applications is already developed, respectively considerably simplified and improved compared to the methods known from the prior art. Hence, with the method according to the invention, a body part of a patient provided with a graphic marker can be localized in the three-dimensional space with respect to its spatial position as well as with respect to its angular position, and to a great extent independent of location and placement of the image recording camera, and without the necessity of the camera calibration before start of the measurements.

Thereby the accuracy of the localization of the graphic marker or the object to be observed, respectively, is already considerably improved compared to the prior art, in that the method according to the invention not only allows statements about the position or the deflection, respectively, of the graphic marker compared to the optical axis of the image recording camera, but also provides the distance between the object or the graphic marker, respectively, and the image recording camera. Based on the thereby always known distance between the object and the image recording camera, not only just qualitative or approximate statements can be made, but place and location of the object can be determined quantitatively in three-dimensional space with high accuracy.

With the background of the additional determination of movement sequences, it is further provided according to a particularly preferred embodiment of the method according to the invention that for recording of a location change of the graphic marker or the body part, respectively, the process steps b) to g) are recurring. In this manner successive images of the body part comprising the graphic marker are generated, with the successive evaluation thereof by the processor device, movement sequences or movement curves, respectively, of the graphic marker or the body part, respectively, can be generated.

According to a further embodiment of the method according to the invention, in case of at least two relative movable body parts, in each case at least one graphic marker is connected with each of the relative movable body parts. In this manner, the relative position of the respective body parts, respectively the relative positions and relative movements between the body parts, can be determined and traced with high reliability and accuracy. According to a further embodiment it is provided, however, that with one and the same body part at least two graphic markers are connected. In this manner, the position of the body part and also the location of the body part in three-dimensional space can be determined with a particularly high accuracy. The latter applies particularly in the case when a known geometrical relation, for example the known distance between the at least two graphic markers, is also considered in the evaluation by the processor device.

According to a further embodiment of the method according to the invention at least two image recording cameras are provided. Here, according to an embodiment, the recording of one and the same graphic marker takes place by means of at least two image recording cameras. In this manner, the reliability and accuracy of the determination of the position or the location, respectively, of the graphic marker in the three-dimensional object space can be further increased.

According to a further embodiment, however, with at least one body part two graphic markers are connected, wherein each of the graphic markers is associated to different, preferably Cartesian or orthogonal, respectively, space directions, and wherein for each of the space directions a separate image recording camera is provided. In this manner, the determination of the position or angular position, respectively, or the recording of a movement sequence of the body part in three-dimensional space can take place with yet further increased accuracy.

As already illustrated at the beginning, the method according to the invention is suitable for a variety of different application areas in which the knowledge about absolute position, relative position or about the movement sequences of body parts is of great interest. According to particularly preferred embodiments of the method according to the invention, the determined position data, however, are provided for orthopedic or dental purposes, for example for exact registration of jaw movements. The invention can be used particularly advantageously in these fields, in particular insofar as the previously used, mostly electromechanical methods and recording devices are often associated with an extremely high expenditure of equipment, and corresponding high cost, as well as with relative high strain on the patient side.

The invention can further be realized independent of how the used graphic marker or the plurality of graphic markers, respectively, is actually formed or which known geometrical characteristics the graphic marker comprises, respectively, as long as at least a sufficient contrast exists that allows the capturing and automatic evaluation of the recordings from the image recording camera by the processor device. According to a particularly advantageous embodiment of the present invention, the graphic marker comprises, however, a majority or plurality of geometrical elements, such as for example, but not in any way exclusively, lines, blocks, circles or ellipses, wherein each of the geometrical elements has at least one known and defined geometrical reference with respect to a fixed point of the graphic marker.

Due to the known and defined geometrical reference of the individual components of the graphic marker, for example due to the characteristic dimensions, shapes and/or relative positions of the individual geometrical elements of the graphic markers to each other, the accuracy of the camera calibration between image space and object space and also the accuracy of the detection of the position or location, respectively, of the graphic marker in the object space, can further be increased considerably.

This is associated with the fact that each geometrical element of the graphic marker, which is additionally recognized by the processor device, can contribute due to its known dimensions or due to its known relative position, respectively, with respect to an also known fixed point of the graphic marker, to the accuracy of the localization of the graphic marker in the image space, and hence also to the improvement of the accuracy of the camera calibration. Another advantageous effect of this embodiment is that due to the additional geometrical elements and the thereby given characteristic shape of the graphic marker, a faster and easier automatic identification and localization of the graphic marker within the image file provided by the image recording camera is possible.

It became apparent that with a suitable design of the graphic marker, particularly with a realization of the graphic marker comprising a plurality of geometric elements, for example with a plurality of (additional) line segments, the accuracy of the position determination of the graphic marker in the image space, and hence the accuracy of the camera calibration and the position determination of the graphic marker in the object space, can be increased almost as desired. This results in particular to the crucial advantage that the physical resolution of the image recording camera does not represent a limiting factor any more for the accuracy of the position determination of the graphic marker. In fact, by means of a suitable design of the graphic marker or by means of a suitable arrangement of the geometrical elements of a graphic marker, respectively, an accuracy of the position determination can be achieved which reaches far into the sub-pixel range of the image recording camera or exceeds the physical resolution of the image recording camera by far, respectively.

This means that the method according to the invention, by means of an appropriate formation of the graphic markers suits the most demanding measurement tasks as they occur, for example, but by no means exclusively, in case of the determination of dental or dental-technical-related position and movement data of the jaws. By means of a suitable implementation and design of the graphic markers, relatively inexpensive image recording cameras therefore can be used without the risk that the limited physical resolution of the same would represent a limitation for the achievable measuring accuracy.

According to a further embodiment of the method according to the invention, information units are coded based on a characteristic arrangement of the geometrical elements of the graphic marker relative to each other or relative to a fixed point, respectively, of the graphic marker. In this manner a multiple advantage of the geometric elements of the graphic markers can be achieved as the geometrical elements serve for increasing of the accuracy of the camera calibration and the position determination of the graphic markers, and also can be used for information storage. For example, by means of a suitable characteristic arrangement of some or all geometrical elements of a graphic marker—for an easier automatic association by the processor device—an identification number of the respective graphic marker can be coded, or characteristic dimensions of the respective graphic marker can be stored in this manner.

The method according to the invention can be realized independent of the manner in which the graphic marker is connected with the associated body part of the patient. According to an embodiment of the method according to the invention it is provided in this context, however, that the graphic marker is connected with an area of the surface by friction lock or adhesion lock. In this manner, a connection between the graphic marker and the body part can be realized particularly simple, for example by forming the graphic marker as a sticker to be placed on the skin or cloth or, for example, by connecting the graphic marker to a stocking-like textile structure, which is slipped over the respective body part.

With this background, according to a further embodiment of the method according to the invention, it is provided that a correction of the determined measuring data is carried out based on collected empirical values for the shifting between the skin surface and the skeleton and which empirically arises depending on the relative position of the body parts in question. In this manner, the measuring accuracy can be increased in cases in which the graphic markers for reasons of simplicity are glued onto the body surface, and hence are not connected with the skeleton.

According to a further preferred embodiment of the method according to the invention, however, at least one graphic marker is connected with a part of the skeleton. In this manner a particularly high measuring accuracy can be achieved because the errors caused by shifting of the skin with respect to the skeleton thereby are eliminated. It is particularly preferable that the graphic marker is connected with at least one tooth of the upper jaw or the lower jaw, respectively. Hence the exact position data or movement data, respectively, of the human skull or head can be determined. Furthermore, in this manner, the data of the relative position and relative movement of the upper jaw and the lower jaw, which are in particular important for dental and dental-technical purposes, can be determined with the required high accuracy.

According to a further particularly preferred embodiment of the method according to the invention, the location of the jaw joint axis in three-dimensional space or the location of the condyles, respectively, hence the joint heads of the lower jaw, is determined automatically by the processor device from the determined data regarding the position and movement of the lower jaw or regarding the relative position and relative movement between the upper jaw and the lower jaw, respectively. This is advantageous insofar as in this manner, the complicated manual determination of the location of the jaw joint axis, which in addition is faulty and only allows a location determination with medium accuracy, is eliminated and replaced by the automatic location determination of the jaw joint axis. The knowledge about the location of the jaw joint axis is of great importance in many areas of dental diagnosis, since diverse data relevant for diagnostic and dental purposes with respect to the jaw movement and the occlusion often use the jaw joint axis and the condyles of the lower jaw as a reference.

With this background it is particularly preferably provided that the determined position or movement data of the lower jaw, respectively the relative position or relative movement data between upper jaw and lower jaw, by means of a coordinate transformation by the processor device, are automatically referenced to a point located on the jaw joint axis. In this manner a uniformity of the obtained data and an associated standardized data usability are ensured. Additionally, the comparison of the data obtained in this manner about the movement sequence of the lower jaw, with similar data, which, however, were generated, for example, in a conventional way with a mechanical or electronic pantograph known from the prior art, is made easier in this manner. A further advantage of this embodiment is that the graphic markers, due to the automatic transformation of the measuring data onto a point located on the jaw joint axis, can to a large extent be placed freely and at will. The need to place the graphic marker exactly at predetermined points of the jaw is eliminated in this manner, which essentially accommodates the uncomplicated measuring sequence and the quick obtaining of the desired measured values.

According to a further preferred embodiment of the method according to the invention, from the determined position data or movement data, respectively, of the lower jaw, by means of the processor device, relevant diagnostic or dental-technical data such as condyle axis position and shifting, condyle path inclination and behavior, Bennett angle, side shift and the like, are derived automatically; from the determined relative position or relative movement date of the jaw and by means of known or measured skull data, the location of any point of the lower jaw is determined; or from the determined position and movement data, parameters for adjustment of dental-technical articulators are derived.

Such automated processing of measuring data obtained on the jaw is of great advantage and of crucial importance for the reliable dental or orthodontic analysis and diagnosis, respectively, as well as for cost effective, quick and accurate performance of dental-technical work by the dental technician, as, for example, for the fabrication of dental prosthesis by means of articulators.

The invention can be realized independent of the manner in which the graphic marker is connected with the body part or one of the jaws of the patient, respectively, as long as a simple, reliable and as accurate as possible reproduction of the position or movement, respectively, of the respective body part, is given by the graphic marker. According to a particularly preferable embodiment of the method according to the invention for this, however, a bite plate is arranged by means of a plastic bite compound on the dental arch of the lower jaw. Thereby, the bite plate is connected with the at least one graphic marker. In this manner a simple and easily detachable connection between the dental arch, respectively the lower jaw, and the graphic marker arises, which in addition, due to the freedom of play, allows a highest possible accuracy for the position measurement and movement tracing.

The invention relates further to a device for recording of position, location or movement of at least a part of the body of a patient or a medical instrument. In an initially known manner, taken by itself, the device comprises at least a graphic marker connectable with the object component—hence with the at least one body part of the patient or with the at least one part of the medical instrument—and at least one image recording camera, wherein the image recording camera is arranged and equipped in a manner that with the image recording camera at least one image of the object component comprising the graphic marker can be generated. The recording device comprises further a processor device for automated processing of image information which is contained in the image generated by the image recording camera.

For this purpose, the device can be formed for position or movement tracing of either the body part of the patient or the medical instrument, or for position or movement tracing of the body part of the patient as well as of the medical instrument. In particular, in the latter case thereby statements can be made about the relative position or relative movement, respectively, between the body part of the patient and the medical instrument, which are especially of importance during manual or automated surgical interventions.

According to the invention, the recording device distinguishes itself in that at least one geometrical size characteristic of the graphic marker is known and receivable in a storage of the processor device. For this purpose, the processor device is equipped for determination of position, angular position and/or the movement path of the graphic marker relative to the image recording camera by means of the known size characteristic and by means of the dimensions thereof in the image space.

In other words, this means with that the device according to the invention distinguishes itself by an automatic camera calibration, wherein the camera calibration takes place automatically by means of known information about the dimensions of the graphic marker.

Compared to the prior art, thanks to the device according to the invention, the localization or the movement tracing, respectively, of the object components, therefore of the parts of a body or of a medical instrument, respectively,—in particular due to the automatic camera calibration—can hence basically be considerably simplified. Furthermore, the device according to the invention allows the determination of the position in three-dimensional space as well as, if necessary, the detection of the angular position of the object component or the graphic marker, respectively, connected with the object component relative to the image recording camera. Thanks to the device according to the invention, for example, a body part of a patient provided with a graphic marker or a medical instrument can hence be localized in three-dimensional space with regard to its spatial position as well as with regard to its angular position.

The accuracy of the localization is in particular considerably improved already compared to the prior art in that the method according to the invention not only allows statements about the position of the graphic marker compared to the optical axis of the image recording camera, but also provides the distance between object or graphic marker, respectively, and image recording camera.

According to a preferred embodiment, the recording device according to the invention distinguishes itself in that at least two graphic markers are provided, wherein for the case of at least two relative movable body parts or object components, respectively, in each case at least one graphic marker is associated to each of the relative movable object components. In this manner also the relative position of the object components, respectively the relative movements between the object components, for example, between two different body parts or between two different limbs of an extremity, can be determined with high reliability and accuracy.

A further embodiment provides that to one and the same object component at least two graphic markers are associated. Therefore, with the recording device, the position of the object component as well as the location of the object component in three-dimensional space can be determined with particularly high accuracy. This applies in particular then, when the processor device is equipped in a manner that the known geometrical relation—for example, the known distance between the two graphic markers—can also be included in the evaluation by the processor device.

According to a further embodiment of the recording device, at least two image recording cameras are provided. Here the image recording cameras according to an embodiment are equipped in a manner that one and the same graphic marker can be recorded by the at least two image recording cameras. In this manner the reliability and accuracy of the position determination or location determination, respectively, in the three-dimensional object space is further increased.

According to a further embodiment of the recording device according to the invention, to at least one object component, however, at least two graphic markers are associated, wherein the graphic markers are provided for arrangement in different, preferably Cartesian or orthogonal space directions, respectively, and wherein for each of the space directions a separate image recording camera is provided.

In this manner, the accuracy of the determination of the position or angular position, respectively, or the accuracy of the recording of a movement sequence of the object component in three-dimensional space can be further increased.

The invention is realized independent of how the at least one used graphic marker is concretely formed or which geometrical features the graphic marker comprises, respectively, as long as a sufficient contrast exists, which allows the capturing and automatic evaluation of the recordings from the image recording camera by the processor device. According to a particularly preferred embodiment of the invention, the graphic marker comprises, however, a majority or plurality of geometrical elements such as, for example, blocks, circles or ellipses, wherein each of the geometrical elements comprises at least one known and in each case defined geometrical reference with respect to a fixed point of the graphic marker.

Due to the known and defined geometrical reference of the individual components of the graphic marker—for example due to the characteristic dimensions, shapes and/or relative positions of the individual geometrical elements of the graphic markers to each other—the accuracy of the camera calibration between image space and object space and also the accuracy of the detection of the position or location, respectively, of the graphic marker in the object space, can further be increased considerably. A further advantageous characteristic of this embodiment is that due to the additional geometrical elements, a faster and easier automatic identification and localization of the graphic marker in the image file provided by the image recording camera can take place, since a graphic marker formed in such a manner stands out clearly and with a lower likelihood of confusion against the background, respectively against other image elements contained in the image file.

This means that the device according to the invention, by means of appropriate formation of the graphic marker, can be used for demanding measuring tasks with the highest requirements in accuracy, as this is—for example—the case in the orthodontic diagnosis or during the determination of relevant dental or dental-technical position and movement data of the jaws, respectively. By means of a suitable implementation and design of the graphic markers, relative inexpensive image recording cameras therefore can be used without the risk that the limited physical resolution of the same would represent a limitation for the achievable measuring accuracy.

According to a further embodiment of the device according to the invention, information units are coded based on a characteristic arrangement of the geometrical elements of the graphic marker relative to each other or relative to a fixed point of the graphic marker, respectively. In this manner, a multiple advantage of the geometrical elements of the graphic markers can be achieved as the geometrical elements serve for increasing of accuracy of the camera calibration and the position determination of the graphic markers, and also can be used for information storage. For example, by means of a suitable characteristic arrangement of some or all geometrical elements of a graphic marker—for an easier automatic identification by the processor device—a separate identification number for each graphic marker can be coded, or characteristic dimensions of the respective graphic marker, in the pattern of the graphic marker itself, can be stored in this manner.

The invention can be realized independent of the manner in which the graphic marker is connected with the associated object component, therefore with the associated body part of the patient, or with the associated part of the medical instrument. According to an embodiment of the invention, the device is equipped for a friction lock or adhesion lock connection of the graphic marker with an area of the object surface. In this manner, a connection between the graphic marker and the object component can be realized particularly simple and quick, for example by forming the graphic marker as a sticker to be placed on the skin, cloth or instrument, or, for example, by connecting the graphic marker to a stocking-like textile structure, which is slipped over the respective body part.

According to a further preferred embodiment of the recording device according to the invention, the device is equipped for connection of the graphic marker with a part of the skeleton. In this manner a particularly high measuring accuracy can be achieved, in particular because the errors caused by shifting of the skin with respect to the skeleton thereby are eliminated. With this background, the device comprises, according to a further embodiment, a mounting arrangement for connecting the graphic marker with at least one tooth of the upper jaw or the lower jaw. In this manner, exact position data or movement data, respectively, of the human skull or head can be determined. Furthermore, in this manner, the data of the relative position and relative movement of the upper jaw and the lower jaw, which are in particular important for dental and dental-technical purposes, can be determined with the required high accuracy.

The device according to the invention can be used regardless of a defined relation or mechanical fixation between the device and the body of the patient or the medical instrument, respectively, exists or not. Thus it is in particular possible to determine and trace relative movements between the different object components with high accuracy, without any defined mechanical connection between the recording device and the traced object or patient, respectively, being present.

According to a preferred embodiment of the invention, the recording device comprises, however, a mechanism for fixation of the at least one image recording camera relative to a part of the body or skeleton, respectively, of the patient. In particular for the case of usage of the recording device according to the invention in the field of the dental analysis and diagnosis, such a fixation between the image recording camera and the patient can be carried out, for example, in the form of a belt, a specific head rest or an elastic clamp, wherein belt, head rest or clamp are applied on the skull, respectively head, of the patient.

In this manner, the head or the skull bone of the patient, respectively, and therefore also the upper jaw, is brought in a defined and temporarily fixed relative position to the recording device or image recording camera, respectively, connected with the belt, head rest or clamp. This serves on the one hand for simplification of the performance of the measuring process and on the other hand for the further increase of the measuring accuracy. In addition, the application of graphic markers on the upper jaw or in the area of the skull or head of the patient, respectively, can hence be abandoned.

According to a further preferred embodiment, the recording device is connectable with a display unit. For this purpose, the processor unit or display unit, respectively, are equipped in such a manner that by means of the determined position, location and/or movement path of the at least one graphic marker, diagnostically relevant data and relations, such as condyle axis position and shifting, condyle path inclination and course, Benett angle, side shift or Posselt schema, can be automatically determined or displayed graphically or numerically, respectively.

The automatic processing and display of the measuring data obtained on the jaw is crucial during the dental or orthodontic analysis and diagnosis, respectively, as well as during the performance of dental-technical work—as, for example, during the fabrication of dental prosthesis by means of an articulator—by the dental technician.

With this background it is further provided according to another embodiment of the invention that the recording device is equipped for automatic determination of characteristic parameters for the immediate adjustment of different types of dental-technical articulators. In this manner, the relevant orthodontic or dental data, respectively, determined with the recording device according to the invention can be transferred reliably with minor expenditure to each articulator used by the dental technician.

Hereafter the invention is described in detail by means of a drawing illustrating only an exemplary embodiment.

In the only FIGURE shows

FIGURE a not-to-scale schematic illustration of an embodiment of a device according to the invention in an isometric view.

In the FIGURE an embodiment of a recording device according to the present invention is illustrated in a highly schematic manner. The recording device illustrated in the FIGURE is provided for use particularly in the dental practice and serves for the so-called lower jaw registration or for the associated recording of the movement paths of the lower jaw, respectively, when opening the mouth, during occlusion movements and the like.

To begin with, the head 1 of the patient can be seen, which is fixed by means of an elastic, cushioned clamp 2 relative to a base 3 of the recording device. Instead of the cushioned clamp 2, for example, a specific head rest can also be used, wherein in this case the recording device is preferably connected with the head rest or the head portion, respectively, of a treatment chair of the dental practice.

At the base 3 of the recording device, besides the cushioned clamp 2 for fixation of the head 1 of the patient, an adjustable camera bracket 4 is arranged. At the camera bracket 4 of the illustrated embodiment, three highly schematically sketched image recording cameras 5, 6, 7 are arranged, the lenses 8 of which at first are pointing approximately towards the patient. Preferably conventional and inexpensive CCD cameras with, for example, USB or Firewire interface can be used here. The image recording cameras 5, 6, 7 are variably attached to the camera bracket 4 so that the most spacious adjustability of the image recording camera 5, 6, 7 relative to the base 3 of the recording device, respectively relative to the patient's head 1, is given.

The patient carries a bite plate (not shown in the FIGURE) in the mouth, which is connected with the teeth of the lower jaw by means of a plastic bite compound and hence follows all movements of the lower jaw. With the bite plate a number of marker areas 9 is connected. With respect to the mouth of the patient in anterior position, the marker areas 9 are arranged on a square rod 10, wherein the square rod 10 in turn is connected with the bite plate arranged in the mouth of the patient. Laterally with regard to the head 1 of the patient in the approximate region of the jaw joints, further marker areas 9 are located, which in the illustrated embodiment are formed in the form of the surfaces of angle profiles 11. Here the angle profiles 11 comprising the lateral marker areas and the square rod 10 carrying the anterior marker areas are coupled by means of a light connection bow 12, which is easily removable from square rod 10.

On each of the marker areas 9, in the anterior 10 as well as in the lateral region 11, a number of graphic markers or markers 13, respectively, are arranged. For reasons of simplicity and presentability, the markers 13 in the illustrated exemplary embodiment are illustrated as simple black circles.

Apart from the cushioned clamp 2 or a corresponding head rest, respectively, and the bite plate including the marker areas 9 connected thereto, unlike the prior art, no further devices, measuring brackets, sensor holders or the like to be connected with the head 1 of the patient are required. This results in fundamental advantages with respect to the performance of the registration of the lower jaw executed according to the invention, which is fast and uncomplicated for the user and hardly stressful for the patient.

For measuring the movement paths of the lower jaw of the patient, the image recording cameras 5, 6, 7 are oriented by means of a corresponding displacement of the camera bracket 4 or by means of a displacement of the individual cameras 5, 6, 7, respectively, relative to the camera bracket 4 such that the visual field of each camera 5, 6, 7 captures a number of graphic markers or markers 13, respectively. In this state, the image files or pixel images, respectively, generated by the image recording cameras 5, 6, 7 are evaluated in regular time intervals by the processor device 14 according to the invention.

In the illustrated embodiment, the measurement can either take place close to the jaw joint by recording and tracing of the lateral marker areas and graphic markers arranged on the angle profiles 11, or a measurement can take place by means of the frontal pin or square rod 10, respectively, by pointing the image recording cameras 5, 6, 7 towards the marker areas arranged anterior on the square rod 10. For the measurement with the frontal pin, therefore, the connection bow 12 with the marker areas and graphic markers arranged close and lateral at 11 to the jaw joint is not needed and can hence be removed together with the angle profiles 11, which, concerning the equipment, results in an extremely simple measuring system including only a bite plate and square rod 10, which is virtually stress-free for the patient.

The measurement takes place each time in such a manner that the processor device 14, by means of an image recognition algorithm, checks the image files or pixel images, respectively, provided by the image recording cameras 5, 6, 7 for the images of the graphic markers or markers 13, respectively, contained in each of the pixel images and subsequently automatically determines, by means of the method according to the invention, the position of the graphic markers or markers 13, respectively, found in the pixel images in three-dimensional space.

Since, according to the invention, the absolute position of the graphic markers in three-dimensional space relative to each of the associated cameras 5, 6, 7 can be determined and since, furthermore, the method according to the invention and the device according to the invention allow an accuracy of the position tracing of the graphic markers which reaches far into the sub-pixel range of the image recording cameras 5, 6, 7, the illustrated device allows the registration or recording, respectively, of the movements of the lower jaw with an accuracy virtually previously not achieved by the prior art.

This is firstly associated in particular with the fact that according to the invention an automatic calibration of the image recording camera 5, 6, 7 takes place, whereby the processor device 14, by means of the dimensions of the graphic markers or marker 13, respectively, determines on the pixel image provided by the respective camera 5, 6, 7 and by means of the known geometry data or by means of the real dimension data of the graphic markers in the object space, respectively, the actual distance between the respective graphic marker and the associated image recording camera 5, 6, 7. Furthermore, this automatic calibration of the image recording cameras 5, 6, 7 by the processor device 14 can be continuously renewed—for example even within the processing of each individual single image—so that at each point in time the exact distance between image recording camera 5, 6, 7 and the graphic marker or marker 13, respectively, is known.

By means of the hereby determined known distance between the graphic marker or marker 13, respectively, and the associated image recording camera 5, 6, 7, however, the absolute position of the graphic marker relative to the image recording camera 5, 6, 7 can be determined in consideration of the imaging properties of the camera lens. This is one of the crucial differences compared to the prior art, where either absolute measurements are completely abandoned, whereby primarily qualitative statements about the recorded movement paths are possible, or where a complicated manual calibration of the used cameras or sensor systems is required.

Another crucial factor of the extremely high accuracy of the localization and the tracing of the graphic markers or markers 13, respectively, achieved with the illustrated recording device is that by means of suitable formation of the graphic markers, the accuracy of the position tracing can be increased almost as desired. For this, in the illustrated embodiment, besides the known diameter of the individual markers 13, for example, the known distance between respectively two markers 13 arranged on the same marker area 9 is also used. Already, with the additional utilization of the known distance between the markers 9 arranged in pairs, the accuracy of the camera calibration can be increased and the precision of the localization and the tracing of the graphic markers can be improved by further orders right into the micrometer range.

This is in particular associated with the fact that each known geometrical feature and each known dimension of the graphic marker increases the accuracy of the localization and the tracing of the graphic marker within the image file provided by the image recording camera 5, 6, 7. By each additional geometrical feature of the graphic marker, the information content of the image of the graphic marker, which is evaluable by means of appropriate image recognition algorithms (for example Hough transformation), is increased; and additionally in each case an accordingly increased number of image information, for example, image pixels is available, which hence can be used for an even more accurate localization of the graphic marker.

For recording of the complete movement sequence of the lower jaw, in the illustrated exemplary embodiment, the marker areas 9 with a graphic marker arranged thereon, which are arranged in the anterior mouth region on the rod 10, and, in principal, only a single one of the three presently used image recording cameras 5, 6, 7 would be already sufficient. The additional marker areas, which are arrangeable in the lateral head area in the region of the jaw joints 11, or the graphic markers, respectively, and the presently used number of three image recording cameras 5, 6, 7, hence serve mainly for the increase of the accuracy during the movement tracing of the lower jaw. Thereby, the image recording camera 7 arranged in the upper area of the camera bracket serves mainly for the accurate recording of the lateral movements, hence the side shift behavior of the lower jaw, which normally occurs with mouth opening movements.

Furthermore, the connection bracket 15 visible in the front region of the recording device serves for the simple adjustment of the rotation position of the two lateral cameras 5 and 6, wherein the connection bracket can be removed after completed adjustment of the cameras 5 and 6 to allow free access to the patient 1. The adjustment of the rotation position of the lateral cameras 5 and 6 serves for setting the obtained measuring data or movement curves, respectively, of the lower jaw in relation to the actual position of the skull or head 1 of the patient, respectively.

Thereby the camera adjustment of the lateral cameras 5 and 6 takes place in a manner that the lateral-arranged image recording cameras 5 and 6 are pivoted or rotated, respectively, by means of the connection bracket 15 around the camera axis until the connection bracket 15 and hence a respectively defined horizontal axis of the camera 5, 6 is oriented in parallel to the Frankfurt horizontal, thus to the virtual connection line between the porion (the upper margin of the external auditory meatus) and the orbital cavity (osseous eye socket).

Apart from the processor device 14, the illustrated recording device or registration device, respectively, comprises further, or is connected with, respectively, an output device 16, for example a monitor and/or a printer, a control panel 17, for example, a keyboard, an (external) storage device 18, for example a USB memory stick, and a data connection to an external computer 19, for example a personal computer, in particular to be able to carry out further detail evaluation of the determined measuring data thereon.

As a result it hence appears that by means of the invention the possibilities for recording or tracing, respectively, of position, location or movement of parts of the body of a patient or a medical instrument, respectively, can be drastically broadened and at the same time also simplified. The invention thereby allows a high degree of automation as well as a high measuring accuracy during the position determination and the movement tracing, wherein at the same time the equipment expenditure is dramatically reduced and the reaction to the object or the body part to be measured or the patient, respectively, is minimized.

The invention hence provides a crucial contribution for improvement of absolute and relative positions or movements, respectively, particularly in fields, such as for example, in the manual or automated surgery or in the dental jaw registration, where highest measuring accuracy and a simple applicability represent central application criteria.

The invention claimed is:

1. A method for recording of three-dimensional position, location or movement of at least one part of a body of a patient arranged in an object space by means of electronic image recognition using at least one image recording camera, whereby position, location or movement is recorded three-dimensionally independently by each one image recording camera, the method comprising the following process steps:
   a) Connecting at least one movable graphic marker with at least one body part, wherein at least one geometrical size characteristic of the graphic marker is known;
   b) Generating an image of at least the area of the body part containing the graphic marker with each image recording camera;
   c) Transferring the image of each image recording camera as an image file into an electronic processor device;
   d) In the image space of each image file, localizing the image of the graphic marker contained in the image file by means of application of an automated image recognition procedure to the image file;

e) Determining the size characteristic of the graphic marker in each image space;
f) Calibrating the recording system by determining three-dimensional absolute position data of the graphic marker in the object space directly relative to each one image recording camera by means of calculating distance and angle between the graphic marker and the respective image recording camera using the size characteristic of the graphic marker in the image space as determined by the respective image recording camera and the known size characteristic of the graphic marker in the object space together with the imaging properties of the respective camera lens;
g) Transferring the determined data regarding the three-dimensional absolute position of the graphic marker in the object space into a data storage wherein at least steps b) to f) are carried out independently for each camera and its respective image.

2. The method according to claim 1, characterized in that for recording of a location change of the graphic marker or a movement sequence of the body part, respectively, the process steps b) to g) are repeated.

3. The method according to claim 1, wherein at least one graphic marker is connected with each of at least two relative moveable body parts.

4. The method according to claim 1, characterized in that with the at least one body part at least two graphic markers are connected.

5. The method according to claim 1, characterized in that at least two image recording cameras for recording of images of the at least one graphic marker are provided.

6. The method according to claim 5, characterized in that with at least one body part at least two graphic markers associated to different space directions are connected, wherein for each of the space directions a separate image recording camera is provided.

7. The method according to claim 6, characterized in that the different space directions correspond to an Cartesian coordinate system.

8. The method according to claim 1, characterized in that the determined position data are used for orthopedic or dental purposes or for registration of lower jaw movements, respectively.

9. The method according to claim 1, characterized in that the graphic marker comprises a majority or plurality of geometrical elements, wherein each of the geometrical elements has at least one known, defined geometrical reference to a fixed point of the graphic marker.

10. The method according to claim 9, characterized in that by means of a characteristic arrangement of the geometrical elements relative to each other and/or relative to a fixed point of the graphic marker, information units are coded.

11. The method according to claim 1, characterized in that the graphic marker is connected with an area of the surface of the body part by friction lock or adhesion lock.

12. The method according to claim 11, wherein at least one graphic marker is connected with each of at least two relative movable body parts, and depending on the determined relative position of the at least two body parts, a correction of the determined measuring data takes place by means of empirical values for the shifting between the skin surface and the skeleton occurring in dependency of the relative position of the body parts.

13. The method according to claim 1, characterized in that the graphic marker is connected with a part of the skeleton.

14. The method according to claim 1, characterized in that the graphic marker is connected with at least one tooth of the upper or lower jaw.

15. The method according to claim 14, characterized in that by means of the processor device, the location of the jaw joint axis or the condyles, respectively, is determined automatically from the determined position or movement data of the lower jaw.

16. The method according to claim 15, characterized in that the determined position or movement data of the lower jaw are related by means of a coordinate transformation to a point located on the jaw joint axis.

17. The method according to claim 14, characterized in that by means of the processor device, relevant dental or dental-technical data, respectively, such as condyle axis position and shifting, condyle path inclination and behavior, Bennett angle, side shift and the like, are derived automatically from the determined position or movement data.

18. The method according to claim 14, characterized in that by means of the processor device, from the determined position and movement data as well as by means of skull data, the location of any point of the lower jaw is determined.

19. The method according to claim 14, characterized in that by means of the processor device, from the determined position or movement data, parameters for adjustment of dental-technical articulators are derived.

20. The method according to claim 14, characterized in that a bite plate is arranged on the dental arch of the lower jaw by means of a bite compound, wherein the bite plate is connected with at least one graphic marker.

21. A device for recording of position, location or movement of at least a component of the body of a patient or a medical instrument, the device comprising at least one movable graphic marker connectable with the object component and at least one image recording cameras, wherein each image recording camera is equipped for generation of at least one image of the object component comprising the graphic marker, the device further comprising a processor device for automated processing of image information contained in the image, characterized in that
at least one geometrical size characteristic of the graphic marker is known and transferable in a storage of the processor device, wherein the processor device is equipped for determination of position, location and/or movement path of the graphic marker three-dimensionally directly relative to each image recording camera independently for the image(s) of each image recording camera by means of the known size characteristic as well as by means of its dimensions in the image space.

22. The device according to claim 21, characterized by at least two graphic markers, wherein each of the graphic markers is associated to respectively one of the at least two relative-movable object components.

23. The device according to claim 21, characterized by at least two graphic markers, wherein the at least two graphic markers are associated to the same object component.

24. The device according to claim 21, characterized by at least two image recording cameras for recording of images of the at least one graphic marker.

25. The device according to claim 21, characterized in that to at least one object component at least two graphic markers arranged in different space directions are associated, wherein the device comprises a separate image recording camera for each space direction.

26. The device according to claim 25, characterized in that the different space orientation corresponds to a Cartesian coordinate system.

27. The device according to claim 21, characterized in that the graphic marker comprises a majority or plurality of geometrical elements, wherein each of the geometrical elements in the object space has at least one known, defined geometrical reference to a fixed point of the graphic marker.

28. The device according to claim 27, characterized in that by means of a characteristic arrangement of the geometrical elements relative to each other and/or to a fixed point of the graphic marker, information units are coded.

29. The device according to claim 21, characterized in that the device is equipped for a friction lock or adhesion lock connection of the graphic marker with an area of the body surface.

30. The device according to claim 21, characterized in that the device is equipped for a connection of the graphic marker with a part of the skeleton.

31. The device according to claim 21, characterized in that the device comprises a mounting arrangement for connection of the graphic marker with at least one tooth of the upper or lower jaw.

32. The device according to claim 21 characterized in that the device comprises a mechanism for fixation of the image recording camera relative to a part of the body or skeleton, respectively.

33. The device according to claim 31, characterized in that the processor device is connectable with a display unit, wherein the processor device or the display unit, respectively, is equipped by means of the determined position, location and/or movement path of the at least one graphic marker for automatic determination or for graphical or numerical display, respectively, of dental-relevant relations, such as condyle axis position and shifting, condyle path inclination and behavior, Bennett angle, side shift, Posselt schema and the like.

34. The device according to claim 31, characterized in that the device is equipped for automatic determination of parameters for adjustment of dental-technical articulators.

* * * * *